(12) United States Patent
Komatsu et al.

(10) Patent No.: US 8,410,196 B2
(45) Date of Patent: Apr. 2, 2013

(54) SURFACE-MODIFIED NANODIAMOND AND ITS PRODUCING METHOD

(75) Inventors: Naoki Komatsu, Otsu (JP); Masaaki Ito, Ohtake (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 242 days.

(21) Appl. No.: 12/754,996

(22) Filed: Apr. 6, 2010

(65) Prior Publication Data

US 2010/0261926 A1 Oct. 14, 2010

(30) Foreign Application Priority Data

Apr. 13, 2009 (JP) .................. 2009-097495

(51) Int. Cl.
*C08K 9/04* (2006.01)
*C08K 3/04* (2006.01)
*C08G 59/00* (2006.01)

(52) U.S. Cl. ........ 523/215; 528/408; 977/773; 977/779; 523/205

(58) Field of Classification Search .................. 523/215; 528/408; 977/773, 779
See application file for complete search history.

(56) References Cited

U.S. PATENT DOCUMENTS

| | | | | |
|---|---|---|---|---|
| 3,201,420 | A * | 8/1965 | Fuzesi et al. | 549/372 |
| 2007/0231744 | A1 * | 10/2007 | Sasao et al. | 430/281.1 |
| 2008/0249229 | A1 * | 10/2008 | Lukehart et al. | 524/496 |
| 2010/0116668 | A1 * | 5/2010 | Landau et al. | 205/50 |

FOREIGN PATENT DOCUMENTS

| | | |
|---|---|---|
| JP | 2007-238411 A | 9/2007 |
| JP | 2008-150250 A | 7/2008 |
| JP | 2008-303104 A | 12/2008 |

* cited by examiner

*Primary Examiner* — Tae H Yoon
(74) *Attorney, Agent, or Firm* — Birch, Stewart, Kolasch & Birch, LLP

(57) ABSTRACT

A surface-modified nanodiamond includes a base nanodiamond, and at least one polyglycerol-chain-containing group present on at least a surface portion of the base nanodiamond, in which the polyglycerol-chain-containing group is represented by following Formula (1):

$$-\text{X}-\text{R} \qquad (1)$$

wherein X represents single bond, —NH—, —O—, —COO—, —PH(=O)O—, or —S—; and R represents a polyglyceryl group. X may be single bond or —NH—. The surface-modified nanodiamond is highly soluble or dispersible satisfactorily stably in water and/or polar organic solvents.

7 Claims, No Drawings

SURFACE-MODIFIED NANODIAMOND AND ITS PRODUCING METHOD

BACKGROUND OF THE INVENTION

1. Field of the Invention

The present invention relates to a surface-modified nanodiamond and a production method thereof. The surface-modified nanodiamond is usable in engineering applications such as materials for polishing agents and dressers adopted to chemical mechanical polishing (CMP); plating materials for corrosion-resistant electrodes adopted to fuel cells; materials for forming very hard surface coating layers typically of cutting tools; and highly heat-resistant and highly thermally conductive materials.

2. Description of the Related Art

Nanodiamonds have characteristic properties of small average particle diameters and large specific surface areas, in addition to properties inherent to diamond. Additionally, they are relatively inexpensive and are readily available.

The nanodiamonds have been produced according to an explosion process or high-temperature and high-pressure process. The explosion process yields a nano-sized diamond (nanodiamond) by explosion of trinitrotoluene and hexogen (cyclotrimethylene-trinitramine). The resulting nanodiamond obtained by this process is highly soluble in water, but contains large amounts of contaminated other carbonaceous materials such as amorphous carbon and graphite and is hard to be chemically modified on surface. In contrast, the high-temperature and high-pressure process is a process of holding a material graphite powder at a high temperature of from 800° C. to 2000° C. and a high pressure of from 1 to 10 GPa in the presence of a metal such as iron or cobalt in a hermetically sealed and pressurized vessel to thereby allow the material to undergo phase transfer directly to a diamond. The nanodiamond obtained by this process contains less amounts of contaminated other carbonaceous materials such as amorphous carbon and graphite and have uniform particle diameters, but is poor in solubility or dispersibility and dispersion stability in water and/or organic solvents. These problems retard the development of new applications of nanodiamonds.

There have been attempted to chemically modify the surfaces of nanodiamonds in order to improve the solubility and dispersibility in water and/or organic solvents (see Japanese Unexamined Patent Application Publication (JP-A) No. 2007-238411; Japanese Unexamined Patent Application Publication (JP-A) No. 2008-303104; and Japanese Unexamined Patent Application Publication (JP-A) No. 2008-150250. The resulting nanodiamonds, however, are not always satisfactorily soluble or dispersible highly stably in water and/or polar organic solvents.

SUMMARY OF THE INVENTION

Accordingly, an object of the present invention is to provide a highly dispersible surface-modified nanodiamond that is satisfactorily soluble or dispersible and dispersible highly stably in water and/or polar organic solvents. Another object of the present invention is to provide a method for producing the surface-modified nanodiamond.

After intensive investigations, the present inventors have found that the modification of the surface of a nanodiamond with a specific group containing a polyglycerol chain remarkably improves the solubility or dispersibility and dispersion stability of the resulting nanodiamond in water and/or polar organic solvents. The present invention has been made based on these findings.

Specifically, the present invention provides, in an embodiment, a surface-modified nanodiamond which includes a base nanodiamond; and at least one polyglycerol-chain-containing group present on at least a surface portion of the base nanodiamond, the at least one polyglycerol-chain-containing group represented by following Formula (1):

$$-X-R \qquad (1)$$

wherein X represents one member selected from the group consisting of single bond, —NH—, —O—, —COO—, —PH(=O)O—, and —S—; and R represents a polyglyceryl group.

X is preferably single bond or —NH—.

In another embodiment, the present invention provides a method for producing a surface-modified nanodiamond. The surface-modified nanodiamond includes a base nanodiamond; and at least one polyglycerol-chain-containing group present on at least a surface portion of the base nanodiamond, the at least one polyglycerol-chain-containing group represented by following Formula (1):

$$-X-R \qquad (1)$$

wherein X represents one member selected from the group consisting of single bond, —NH—, —O—, —COO—, —PH(=O)O—, and —S—; and R represents a polyglyceryl group. This method includes the step of subjecting glycidol to ring-opening addition polymerization with a nanodiamond or with a surface-modified nanodiamond including a base nanodiamond and at least one group present on at least a surface portion of the base nanodiamond and represented by following Formula (2):

$$-X^1-H \qquad (2)$$

wherein $X^1$ represents one member selected from the group consisting of —NH—, —O—, —COO—, —PH(=O)O—, and —S—.

In the production method, glycidol may be subjected to ring-opening addition polymerization with a nanodiamond to give a surface-modified nanodiamond modified on surface with at least one polyglyceryl group.

Independently, a surface-modified nanodiamond modified on surface with at least one polyglycerylamino group may be obtained through the steps of hydrogenating a nanodiamond to give a hydrogenated nanodiamond; aminating the hydrogenated nanodiamond to give an aminated nanodiamond; and subjecting glycidol to ring-opening addition polymerization with the aminated nanodiamond.

In contrast to known nanodiamonds, the surface-modified nanodiamond according to an embodiment of the present invention has significantly improved solubility or dispersibility and dispersion stability in water and/or polar organic solvents, can thereby be handled with remarkably improved handleability, and can be used in various uses as a stable solution or dispersion in water or a polar organic solvent or can be subjected to any of chemical reactions and physical reactions in water and/or a polar organic solvent. This gives a nanodiamond material that is usable in engineering applications such as materials for polishing agents and dressers adopted to CMP (Chemical Mechanical Polishing); plating materials for corrosion-resistant electrodes adopted to fuel cells; materials for forming very hard surface coating layers typically of cutting tools; and highly heat-resistant and highly thermally conductive materials.

These and other objects, features, and advantages of the present invention will be more fully understood from the following description of preferred embodiments, in which all numbers are assumed to be modified by the term "about."

DESCRIPTION OF THE PREFERRED EMBODIMENTS

Surface-modified nanodiamonds according to embodiments of the present invention each include a base nanodiamond (nanodiamond matrix) and at least one polyglycerol-chain-containing group represented by Formula (1) present on or linked to (combined to) at least a surface portion of the base nanodiamond. In Formula (1), X represents one member selected from the group consisting of single bond, —NH—, —O—, —COO—, —PH(=O)O—, and —S—; and R represents a polyglyceryl group. Hereinafter the surface-modified nanodiamond according to the present invention is also simply referred to as "ND-X—R", wherein "ND" represents a nanodiamond.

The number-average degree of polymerization "n" of the polyglyceryl group R is not critical, as long as targeted high dispersibility is obtained. However, a polyglyceryl group R, if having an excessively low number-average degree of polymerization "n", may not provide sufficient interparticle repulsive force between nanodiamond particles, may thereby not effectively prevent the aggregation of the nanodiamond particles, and may not contribute to maintain the surface-modified nanodiamond to be dispersed in a solvent stably. In contrast, a polyglyceryl group R, if having an excessively high number-average degree of polymerization "n", may cause entanglement of polyglycerol polymer chains between nanodiamond particles to often cause aggregation of the nanodiamond particles and, in addition, may dilute characteristic properties of the surface-modified nanodiamond as a diamond material. The number-average degree of polymerization "n" of the polyglyceryl group is therefore preferably from 1 to 100, more preferably from 2 to 40, and furthermore preferably from 3 to 20. As used herein the term "number-average degree of polymerization "n"" is defined as the number of glycidol units constituting a polyglycerol chain combined with one surface functional group of the material nanodiamond. The number of surface functional groups of the raw-material nanodiamond can be determined, for example, by carrying out elemental analysis of the material nanodiamond, or by measuring an acid number of the raw-material nanodiamond, or by the both techniques in combination.

X is especially preferably single bond or —NH—.

In a method for producing a surface-modified nanodiamond according to an embodiment of the present invention, glycidol is subjected to ring-opening addition polymerization with a nanodiamond or surface-modified nanodiamond modified on surface with at least one group represented by Formula (2) to give a surface-modified nanodiamond modified on surface with at least one polyglycerol-chain-containing group represented by Formula (1). In Formula (2), $X^1$ represents one member selected from the group consisting of —NH—, —O—, —COO—, —PH(=O)O—, and —S—.

To introduce a modifying group into a nanodiamond (ND), a reagent corresponding to the modifying group may be directly reacted with the nanodiamond, but a preferred process is as follows. Specifically, the nanodiamond is once reduced by heating at 400° C. to 1000° C. in a hydrogen stream to give a hydrogenated nanodiamond (ND-H) (see Japanese Unexamined Patent Application Publication (JP-A) No. 2007-238411), and the hydrogenated nanodiamond is reacted with a reagent corresponding to the modifying group. This process is preferred from the viewpoint typically of introducing the modifying group at a high rate.

The average particle diameter of the nanodiamond (ND) or hydrogenated nanodiamond (ND-H) used as a raw material is generally from 3 to 200 nm, more preferably from 7 to 100 nm, and especially preferably from 10 to 40 nm. The choice of the particle diameter of the raw-material nanodiamond gives a surface-modified nanodiamond having a suitable particle diameter for the intended use. Nanodiamonds of various particle diameters are available by adjusting the process and conditions for the preparation of a nanodiamond from graphite and/or by adjusting conditions of classification operation after the preparation. Independently, nanodiamonds of various particle diameters prepared according to various processes are commercially available from existing manufacturers.

Production of ND-NH—R

Of surface-modified nanodiamonds each modified on surface with at least one polyglycerol-chain-containing group represented by Formula (1), a surface-modified nanodiamond in which X is —NH— (ND-NH—R) can be obtained by introducing amino group to a hydrogenated nanodiamond (ND-H) to give an aminated nanodiamond (ND-$NH_2$); and subjecting glycidol to ring-opening polymerization with the aminated nanodiamond (ND-$NH_2$) according to a common procedure.

The introduction of amino group into the hydrogenated nanodiamond (ND-H) may be carried out typically by heating ND-H at 300° C. to 800° C. in an ammonia stream. The introduction of amino group can also be performed by chlorinating ND-H in a chlorine stream to give a chlorinated nanodiamond before the reaction with ammonia, and reacting the chlorinated nanodiamond with ammonia (see Japanese Unexamined Patent Application Publication (JP-A) No. 2007-238411).

The reaction between the aminated nanodiamond (ND-$NH_2$) and glycidol may be performed, for example, by adding glycidol and a catalyst in an inert gas atmosphere to the system containing the aminated nanodiamond and heating the system at 50° C. to 100° C. The catalyst may be an acidic catalyst or basic catalyst. Exemplary preferred acidic catalysts include trifluoroboron etherate, acetic acid, and phosphoric acid; and exemplary preferred basic catalysts include triethylamine, pyridine, dimethylaminopyridine, and triphenylphosphine.

The conditions of ring-opening polymerization of glycidol can be referred typically to S. R. Sandler et al., J. Polym. Sci., Polym. Chem. Ed., Vol. 4, 1253 (1966); E. J. Vanderberg, J. Polym. Sci., Polym. Chem. Ed., Vol. 23, 915 (1985); and G. R. Newcome et al., Dendritic Macromolecules: Concepts, Syntheses, Perspectives, V C H, Weinheim (1996).

Production of ND-O—R

Of surface-modified nanodiamonds each modified on surface with at least one polyglycerol-chain-containing group represented by Formula (1), a surface-modified nanodiamond in which X is —O— (ND-O—R) can be obtained by introducing hydroxyl group into a hydrogenated nanodiamond (ND-H) to give a hydroxylated nanodiamond (ND-OH), and subjecting glycidol to ring-opening polymerization with the hydroxylated nanodiamond according to the procedure as above.

The introduction of hydroxyl group into ND-H may be carried out, for example, by adding benzoyl peroxide to ND-H in acetic acid and heating the mixture to esterify ND-H to thereby give an esterified ND, and hydrolyzing the esterified ND with an acid or base according to a common procedure.

Production of ND-COO—R

Of surface-modified nanodiamonds each modified on surface with at least one polyglycerol-chain-containing group represented by Formula (1), a surface-modified nanodiamond in which X is —COO— (ND-COO—R) can be produced, for example, in the following manner. A nanodiamond prepared from material graphite through the explosion process or high-temperature high-pressure process is known to have carboxyl groups on its surface due to side reactions occurring in the preparation; and a ND-COO—R can be produced by subjecting glycidol to ring-opening polymerization directly with the carboxyl groups present on the surface of the material nanodiamond according to the procedure as above. Alternatively, the ND-COO—R can also be produced by oxidizing an unsaturated group present on the surface of a material nanodiamond into a carboxyl group, and subjecting glycidol to ring-opening polymerization with the formed carboxyl group. Typically, the ND-COO—R can be produced by dispersing a material nanodiamond in a suitable disperse medium such as methylene chloride, introducing thereinto ozone generated by an ozone generator to cause oxidative cleavage to form an aldehyde group, further oxidizing the aldehyde group with air into carboxyl group, and subjecting glycidol to ring-opening polymerization with the carboxyl group according to the procedure as above.

Production of ND-S—R

Of surface-modified nanodiamonds each modified on surface with at least one polyglycerol-chain-containing group represented by Formula (1), a surface-modified nanodiamond in which X is —S— (ND-S—R) can be produced, for example, in the following manner. Specifically, the ND-S—R is produced by applying an ultraviolet ray (254 nm) to the surface of a hydrogenated nanodiamond (ND-H) to form a free radical, allowing a suitable alkyl mercaptan or dialkyl disulfide to trap the free radical to thereby introduce an alkylthio group onto the surface of the nanodiamond, removing the alkyl moiety with a suitable deprotecting reagent to give a ND-SH, and subjecting glycidol to ring-opening polymerization with the ND-SH according to the procedure as above. For example, the ND-S—R can be produced by reacting bis(4-methoxybenzyl)disulfide with a nanodiamond dispersed in isopropanol with the application of an ultraviolet ray of 254 nm to the nanodiamond to thereby introduce 4-methoxybenzylthio group onto the nanodiamond, converting the 4-methoxybenzylthio group into thiol group by the removal of the methoxybenzyl moiety using a mixture of trimethylsilyl bromide and trifluoroacetic acid (TFA), and subjecting glycidol to ring-opening polymerization with the thiol group according to the procedure as above.

Production of ND-PH(=O)O—R

Of surface-modified nanodiamonds each modified on surface with at least one polyglycerol-chain-containing group represented by Formula (1), a surface-modified nanodiamond in which X is —PH(=O)O— (ND-PH(=O)O—R) can be produced, for example, in the following manner. Specifically, the ND-PH(=O)O—R can be produced by applying an ultraviolet ray (254 nm) to the surface of a hydrogenated nanodiamond (ND-H) to form a free radical, trapping the free radical by an appropriate phosphorus compound to introduce phosphinic acid group onto the surface of nanodiamond, and subjecting glycidol to ring-opening polymerization with the introduced phosphate group according to the procedure as above. Typically, the ND-PH(=O)O—R can be produced by reacting hypophosphorous acid with a nanodiamond dispersed in isopropanol with the application of an ultraviolet ray of a wavelength of 254 nm to introduce phosphinic acid group, and subjecting glycidol to ring-opening polymerization with the introduced phosphinic acid group according to the procedure as above.

Production of ND-R

Of surface-modified nanodiamonds each modified on surface with at least one polyglycerol-chain-containing group represented by Formula (1), a surface-modified nanodiamond in which X is single bond (ND-R) can be produced, for example, by reacting a nanodiamond (ND) directly with glycidol according to the procedure as above. Specifically, carboxyl group and/or hydroxyl group is inherently formed and present on a surface of the nanodiamond during production processes thereof and reacts with glycidol to form ND-R.

The resulting surface-modified nanodiamonds each modified on surface with at least one polyglycerol-chain-containing group represented by Formula (1) can be purified after the completion of reaction by a separation/purification procedure such as concentration, precipitation, centrifugal separation, filtration, extraction, washing, or drying, or by any combination of these separation/purification procedures.

Though not critical as long as targeted high dispersibility is obtainable, the amount of a chemically modifying group to be introduced onto a nanodiamond to give a surface-modified nanodiamond modified on surface with at least one polyglycerol-chain-containing group represented by Formula (1) is such that the amount of chemically modified portions each containing at least one polyglycerol chain is preferably from 4 to 750 parts by weight, more preferably from 9 to 380 parts by weight, and furthermore preferably from 13 to 150 parts by weight, per 100 parts by weight of the nanodiamond-structure matrix (base nanodiamond). A chemically modifying group containing at least one polyglycerol chain, if introduced in an excessively small amount, may not sufficiently cover the surface of the nanodiamond matrix, thereby may not satisfactorily effectively prevent the nanodiamond particles from aggregation, and the resulting nanodiamond may not be dispersed sufficiently stably in a solvent. In contrast, a chemically modifying group, if introduced in an excessively large amount, may dilute the characteristic properties of the resulting surface-modified nanodiamond as a diamond material. The ratio of the amount of chemically modified portions containing at least one polyglycerol chain introduced onto the surface to the amount of the nanodiamond-structure matrix can be determined through the determination of a weight change during heat treatment of the surface-modified nanodiamond using a differential thermogravimetric analyzer (TG-DTA) or through the determination of the ratio in CHNO (carbon, hydrogen, nitrogen, and oxygen) composition between them by elemental analysis.

The resulting surface-modified nanodiamonds each modified on surface with at least one polyglycerol-chain-containing group represented by Formula (1) are highly soluble or dispersible and are highly stably dispersible in water and/or polar organic solvents and are thereby usable in engineering applications such as materials for polishing agents and dressers adopted to CMP; plating materials for corrosion-resistant electrodes adopted to fuel cells; materials for forming very hard surface coating layers typically of cutting tools; and highly heat-resistant and highly thermally conductive materials.

EXAMPLES

The present invention will be illustrated in further detail with reference to several examples below. It should be noted, however, these examples are never construed to limit the scope of the present invention.

Example 1

Preparation of Dry ND

A nanodiamond ND30 having an average particle diameter of 30 nm was obtained from Tomei Diamond Co., Ltd. The nanodiamond ND30 had been prepared according to the method described in Small, vol. 4 (No. 12), p 2154 (2008). The ND30 (60 mg) was placed in a 30-mL eggplant flask, dried at 50° C. at a highly reduced pressure (0.09 mmHg) for 30 minutes, and thereby yielded 44.6 mg of a black powder. This had an acid value of 60.5 KOH mg/g, as determined as the amount of acidic functional groups present on the surface thereof.

Introduction of PGL (polyglycerol) Modifying Group Into Surface Functional Group The dried ND30 (5.00 mg) was placed in a glass reactor, and 2.5 μL of pyridine and 200 μL of glycidol were sequentially added thereto in an atmosphere of argon gas, followed by stirring at 70° C. for 3 hours. The reaction mixture was poured into a 1:3 mixture of methanol and chloroform, subjected to centrifugal separation (15000 rpm, 10 minutes, 20° C.) to remove a supernatant; the procedure of adding a 1:1 mixture of methanol and chloroform to precipitates, stirring and dispersing the resulting mixture, and centrifugal separation (15000 rpm, 10 minutes, 20° C.) of the mixture was repeated a total of two times to remove supernatants; the precipitates were added with and dispersed in methanol with stirring, subjected to the forth centrifugal separation (15000 rpm, 10 minutes, 20° C.) to give black precipitates; the black precipitates were dispersed again in methanol, trapped on a membrane filter with a pore size of 100 μm, dried, and thereby yielded 5.77 mg of a solid substance. The diffuse reflectance infrared spectrum of the substance was measured to find that there were observed a peak derived from nanodiamond skeleton at around 2926 cm$^{-1}$, a peak derived from hydroxyl group of polyglyceryl group at around 3396 cm$^{-1}$, and a peak derived from ether bond of polyglyceryl group at around 1085 cm$^{-1}$. The substance was found to contain C: 79.39%, H: 2.43%, N: 0.3%, and O: 17.74% as a result of elemental analysis, demonstrating that polyglycerol chains were introduced into the original ND30 in an amount of 29.5 percent by weight relative to the weight of the original ND30. The average degree of polymerization of polyglycerol chain per one acidic functional group was determined to find that the polyglycerol chain was 3.7-mer.

Example 2

The product obtained in Example 1 was dispersed in a concentration of 0.25 mg/mL in pure water with the application of ultrasound, filtrated through a membrane filter with a pore size of 100 nm, and thereby yielded a colorless transparent filtrate. Undispersed black solids separated upon the membrane filter were washed with 1 mL of water ten times, dried in vacuo, and weighed to find that the colorless transparent filtrate contained 0.17 mg/mL of the substance dispersed therein. The homogeneous dispersion was left stand at room temperature for one month to find that the dispersion was in a stable state without precipitation.

Example 3

The product obtained in Example 1 was dispersed in a concentration of 0.5 mg/mL in water, dimethylformamide, and dimethyl sulfoxide, respectively, with the application of ultrasound, filtrated through a membrane filter with a pore size of 100 nm, and thereby yielded colorless transparent filtrates. Undispersed black solids separated upon the membrane filter were washed with 1 mL of water ten times, dried in vacuo, and weighed to find that the colorless transparent filtrates as an aqueous dispersion, a dimethylformamide dispersion, and a dimethyl sulfoxide dispersion contained 0.26 mg/mL, 0.22 mg/mL, and 0.27 mg/mL, respectively, of the substance dispersed therein. The homogeneous dispersions were left stand at room temperature for one month to find that the dispersions were each in a stable state without precipitation.

Example 4

The product obtained in Example 1 was dispersed in a concentration of 0.25 mg/mL in a phosphate buffer with the application of ultrasound, filtrated through a membrane filter with a pore size of 100 nm, and thereby yielded a colorless transparent filtrate. Undispersed black solids separated upon the membrane filter were washed with 1 mL of water ten times, dried in vacuo, and weighed to find that the phosphate buffer contained 0.16 mg/mL of the substance dispersed therein. The homogeneous dispersion was left stand at room temperature for one month to find that the dispersion was in a stable state without precipitation.

Example 5

Preparation of Dried ND

A nanodiamond ND4 having an average particle diameter of 4 nm (product name "NanoAmando (registered trademark) B" supplied by NanoCarbon Research Institute Co., Ltd.) was dried under the same conditions as in Example 1 and thereby yielded a black powder.

Introduction of PGL Modifying Group Into Surface Functional Group

The dried ND4 (5.00 mg) was placed in a glass reactor, and 2.5 μL of pyridine and 1.2 mL of glycidol were sequentially added in an atmosphere of argon gas, followed by stirring at 70° C. for 3 hours. The reaction mixture was poured into a 1:5 mixture of methanol and chloroform; subjected to centrifugal separation (15000 rpm, 10 minutes, 20° C.) to remove a supernatant; the precipitates were added with and dispersed in a 1:3 mixture of methanol and chloroform with stirring, subjected to centrifugal separation (15000 rpm, 10 minutes, 20° C.) to remove a supernatant; the procedure of dispersing precipitates in a 1:1 mixture of methanol and chloroform with stirring and centrifugal separation (15000 rpm, 10 minutes, 20° C.) of the dispersion was repeated a total of two times to remove supernatants; the resulting precipitates were added with and dispersed in methanol with stirring, the dispersion was subjected to fifth centrifugal separation (15000 rpm, 10 minutes, 20° C.) to give black precipitates, the black precipitates were dispersed again in methanol, trapped on a membrane filter with a pore size of 100 μm, and thereby yielded 5.14 mg of a dark brown solid substance. The diffuse reflectance infrared spectrum of this substance was measured to find that there were observed a peak derived from nanodiamond skeleton at around 2920 cm$^{-1}$, a peak derived from hydroxyl group of polyglyceryl group at around 3380 cm$^{-1}$, and a peak derived from ether bond of polyglyceryl group at around 1130 cm$^{-1}$. The substance was found to contain C: 87.02%, H: 1.97%, N: 2.24%, and O: 8.82% as a result of elemental analysis, demonstrating that polyglycerol chains were introduced into the original ND4 in an amount of 9.7 percent by weight. The average degree of polymerization of polyglycerol chain per one acidic functional group was determined to find that the polyglycerol chain was 2.3-mer, as the raw-material ND4 had an acid value of 31.9 KOH mg/g.

Example 6

The product obtained in Example 5 was dispersed in a concentration of 0.25 mg/mL in pure water with the application of ultrasound dispersion, filtrated through a membrane filter with a pore size of 100 nm, and thereby yielded a colorless transparent filtrate. Undispersed black solids separated upon the membrane filter were washed with 1 mL of water ten times, dried in vacuo, and weighed to find that the colorless transparent filtrate contained 0.19 mg/mL of the substance dispersed therein. The homogeneous dispersion was left stand at room temperature for one month to find that the dispersion was in a stable state without precipitation.

Example 7

Production of Nanodiamond having Surface Modified with Amino Group

In an electric tubular furnace, 50 mg of a hydrogenated nanodiamond (ND-H; average particle diameter: 30 nm) (ND-30H) (supplied by Tomei Diamond Co., Ltd.) was placed stand, the tubular furnace was raised in temperature to 300° C., and chlorine gas was circulated at a flow rate of 40 mL per minute for 3 hours. Subsequently, the tubular furnace was raised in temperature to 450° C., and ammonia gas was circulated at a flow rate of 40 mL per minute. A reaction was performed for 3 hours while maintaining the tubular furnace at a temperature of 450° C., and thereby yielded 50 mg of a surface-modified nanodiamond modified on surface with amino group (ND30-NH$_2$). This was found to contain C: 96.79%, H: 0.79%, and N: 0.80% as a result of elemental analysis.

Modification of Amino-Surface-Modified Nanodiamond (ND30-NH$_2$) with Polyglyceryl Group The material nanodiamond modified on surface with amino group (ND30-NH$_2$) was dried at 50° C. at a highly reduced pressure (0.09 mmHg) for 30 minutes in the same manner as in Example 1 before subjected to a reaction.

The dried ND30-NH$_2$ (5.00 mg) was placed in a glass reactor, subjected to an ultrasonic treatment at room temperature for 5 minutes in an ultrasonic cleaner (45 kHz) to give a homogeneous dispersion, and 2.5 μL of pyridine and 1.2 mL of glycidol were sequentially added in an atmosphere of argon gas, followed by stirring at 70° C. for 3 hours. The reaction mixture was poured into a 1:3 mixture of methanol and chloroform, subjected to centrifugal separation (15000 rpm, 10 minutes, 20° C.) to remove a supernatant, the procedure of adding and dispersing precipitates in a 1:1 mixture of methanol and chloroform with stirring and the centrifugal separation (15000 rpm, 10 minutes, 20° C.) of the dispersion was repeated a total of two times to remove supernatants, precipitates were added with and dispersed in methanol, the dispersion was subjected to fourth centrifugal separation (15000 rpm, 10 minutes, 20° C.) and thereby yielded black precipitates, the precipitates were dispersed again in methanol, separated through filtration upon a membrane filter with a pore size of 100 μm, and thereby yielded 2.86 mg of a black solid substance.

The diffuse reflectance infrared spectrum of this substance was measured to find that there were observed a peak derived from nanodiamond skeleton at around 2868 cm$^{-1}$, a peak derived from hydroxyl group of polyglyceryl group at around 3365 cm$^{-1}$, and a peak derived from ether bond of polyglyceryl group at around 1095 cm$^{-1}$. The substance was found to contain C: 88.7%, H: 2.3%, N: 0.7%, and O: 8.51% as a result of elemental analysis, demonstrating that polyglycerol chains were introduced into the original ND30-NH$_2$ in an amount of 24 percent by weight. The average degree of polymerization of polyglycerol chain per one amino group was determined and found that the polyglycerol chain was 5.6-mer.

Example 8

The product obtained in Example 7 was dispersed in a concentration of 0.25 mg/mL in pure water with the application of ultrasound dispersion, filtrated through a membrane filter with a pore size of 100 nm, and thereby yielded a colorless transparent filtrate. Undispersed black solids separated upon the membrane filter were washed with 1 mL of water ten times, dried in vacuo, and weighed to find that the colorless transparent filtrate contained 0.20 mg/mL of the substance dispersed therein. The homogeneous dispersion was left stand at room temperature for one month to find that the dispersion was in a stable state without precipitation.

Evaluation Test

ND30-H, ND30-NH$_2$, and the polyglyceryl-group-introduced ND30-NH$_2$ prepared in Example 7 (each 10.0 mg) were placed in vials respectively, each mixed with 1 mL of pure water, subjected to ultrasonic irradiation for 2 minutes, and left stand for one week. The mixtures (dispersions) were thereafter filtrated using a membrane filter with a pore size of 100 nm. Undispersed solid substances separated upon the membrane filter were washed with 1 mL of water ten times, dried in vacuo, and weighed to determine the amounts of substances stably dispersed in pure water. The results are shown in Table 1 below, demonstrating that the nanodiamond bearing introduced polyglyceryl groups shows remarkably improved dispersibility.

TABLE 1

| | Reaction product of Example 7 | ND30-NH$_2$ | ND30-H |
|---|---|---|---|
| Dispersibility in water (mg/mL) | 4.2 | 1.7 | 0.2 |

While the present invention has been described with reference to preferred embodiments thereof, it should be understood by those skilled in the art that various modifications, combinations, subcombinations, and alterations may occur depending on design requirements and other factors insofar as they are within the scope of the appended claims or the equivalents thereof.

What is claimed is:

1. A surface-modified nanodiamond comprising a base nanodiamond and at least one polyglycerol-chain-containing group present on at least a surface portion of the base nanodiamond, the polyglycerol-chain-containing group represented by following Formula (1):

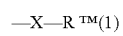

wherein X represents one member selected from the group consisting of single bond and —PH(=O)O—; and R represents a polyglyceral group.

2. The surface-modified nanodiamond of claim 1, wherein X is single bond.

3. A method for producing a surface-modified nanodiamond, the surface-modified nanodiamond including a base nanodiamond; and at least one polyglycerol-chain-containing group present on at least a surface portion of the base, nanodiamond, the at least one polyglycerol-chain-containing group represented by following Formula (1):

—X—R (1)

wherein X represents one member selected from the group consisting of single bond and —PH(=O)O—; and R represents a polyglyceryl group, the method comprising the step of:

subjecting glycidol to ring-opening addition polymerization with a nanodiamond or with a surface-modified nanodiamond including a base nanodiamond and at least one group present on at least a surface portion of the base nanodiamond and represented by following Formula (2):

—$X^1$—H (2)

wherein $X^1$ represents —PH(=O)O—.

4. The method of claim 3, wherein glycidol is subjected to ring-opening addition polymerization with the nanodiamond to give a surface-modified nanodiamond modified on surface with at least one polyglyceryl group.

5. The surface-modified nanodiamond of claim 1, wherein X represents —PH(=O)O—.

6. The surface-modified nanodiamond of claim 1, wherein the number-average degree of polymerization "n" of the polyglyceryl group R is from 2 to 40.

7. The method of claim 4, wherein glycidol is subjected to ring-opening addition polymerization with the nanodiamond in the presence of a catalyst, wherein the catalyst is an acidic catalyst or basic catalyst selected from the group consisting of pyridine and triphenylphosphine.

\* \* \* \* \*